(12) United States Patent
Wang et al.

(10) Patent No.: US 9,464,994 B2
(45) Date of Patent: Oct. 11, 2016

(54) HIGH SENSITIVITY TUNABLE RADIO FREQUENCY SENSORS

(71) Applicant: Clemson University, Clemson, SC (US)

(72) Inventors: Pingshan Wang, Central, SC (US); Yan Cui, Central, SC (US); Yuxi He, Evanston, IL (US); David Moline, Pendleton, SC (US); Jiwei Sun, Central, SC (US)

(73) Assignee: Clemson University, Clemson, SC (US)

( * ) Notice: Subject to any disclaimer, the term of this patent is extended or adjusted under 35 U.S.C. 154(b) by 254 days.

(21) Appl. No.: 14/445,433

(22) Filed: Jul. 29, 2014

(65) Prior Publication Data

US 2015/0035546 A1 Feb. 5, 2015

Related U.S. Application Data

(60) Provisional application No. 61/859,868, filed on Jul. 30, 2013.

(51) Int. Cl.
*G01R 27/04* (2006.01)
*G01N 22/00* (2006.01)
(Continued)

(52) U.S. Cl.
CPC ............ *G01N 22/00* (2013.01); *G06F 1/3203* (2013.01); *G01B 9/02* (2013.01)

(58) Field of Classification Search
CPC .. G01N 21/47; G01N 21/4738; G01N 22/00; G01N 33/49; G01N 33/4915; G01N 33/492; G06F 1/3203; G01R 27/2617; G01R 27/2635; G01R 27/2658; G01R 27/2664; G01R 27/2688; G01R 27/2694; H03H 7/00; H04B 3/04; H04B 3/06; H04B 3/08; B01L 3/502761; B01L 3/502715; B01L 2200/0668; B01L 2300/0654; B01L 2300/0816; B01L 2300/168
USPC ....... 73/61.75, 861; 324/637, 638, 639, 641, 324/642, 646, 653, 659, 663, 667, 692, 324/693; 333/17.1, 174, 176, 235; 356/338, 356/451, 452, 453, 454, 455, 477, 478, 479, 356/480, 481; 435/7.24, 34, 287.1, 287.2, 435/288.7

See application file for complete search history.

(56) References Cited

U.S. PATENT DOCUMENTS 6,452,465 B1  9/2002  Brown et al.
6,828,789 B2  12/2004  Hyde et al.
(Continued)

FOREIGN PATENT DOCUMENTS

EM  2486416  8/2012
EP  1352444  10/2003
(Continued)

OTHER PUBLICATIONS

Newman et al., "A Magneto-Optic Route Toward the In Vivo Diagnosis of Malaria: Preliminary Results and Preclinical Trial Data", Biophysical Journal, vol. 95, No. 2, Jul. 2008, pp. 994-1000.
(Continued)

*Primary Examiner* — Arleen M Vazquez
*Assistant Examiner* — Steven Yeninas
(74) *Attorney, Agent, or Firm* — Dority & Manning, P.A.

(57) ABSTRACT

Highly sensitive and tunable RF sensors that provide detection and analysis of single cells and particles are provided. The tunable RF sensors are configured as tunable interferometers, wherein cells or particles to be analyzed are passed through a channel, such as a microfluidic channel, across waveguides corresponding to reference and test branches of the interferometers. A network analyzer coupled to the interferometers can be configured to measure a plurality of scattering parameters, such as transmission scattering coefficients ($S_{21}$) of the reference and test branches, to evaluate characteristics of cells passing through the channel. A plurality of tunable interferometers may be employed, each interferometer operating in different frequency bands such that information obtain from the plurality of interferometers may be combined to provide further information.

17 Claims, 11 Drawing Sheets

(51) Int. Cl.
*G06F 1/32* (2006.01)
*G01B 9/02* (2006.01)

(56) References Cited

U.S. PATENT DOCUMENTS

| | | |
|---|---|---|
| 7,391,212 B2 | 6/2008 | Maier et al. |
| 7,403,008 B2 | 7/2008 | Blank et al. |
| 7,573,356 B2 | 8/2009 | Kawai et al. |
| 7,586,393 B2 | 9/2009 | de Raed et al. |
| 7,589,604 B2 | 9/2009 | Ninan et al. |
| 7,633,295 B2 | 12/2009 | Tyszka et al. |
| 7,825,754 B2 | 11/2010 | Kawai et al. |
| 8,067,937 B2 | 11/2011 | Blank et al. |
| 8,106,728 B2 | 1/2012 | Ding et al. |
| 8,164,333 B2 | 4/2012 | Rugar et al. |
| 8,214,006 B2 | 7/2012 | Newman et al. |
| 8,269,496 B2 | 9/2012 | Subramanian et al. |
| 8,293,089 B1 | 10/2012 | Bourdon et al. |
| 2006/0165342 A1* | 7/2006 | Pau .................. B01L 3/502715 385/12 |
| 2008/0296175 A1 | 12/2008 | Tanaka |
| 2009/0042241 A1 | 2/2009 | Yu-Chong et al. |
| 2009/0225301 A1* | 9/2009 | Morofke .................. G01P 5/26 356/28.5 |
| 2009/0316151 A1 | 12/2009 | Matula et al. |
| 2011/0227664 A1 | 9/2011 | Wyville |
| 2011/0269221 A1 | 11/2011 | Katsumoto et al. |
| 2012/0120408 A1* | 5/2012 | Yasuno .................. A61B 3/102 356/479 |
| 2012/0135509 A1 | 5/2012 | Hall |
| 2012/0142032 A1 | 6/2012 | Morgan et al. |
| 2012/0212304 A1 | 8/2012 | Koechlin et al. |
| 2012/0214224 A1 | 8/2012 | Chan |
| 2012/0256710 A1 | 10/2012 | Bao et al. |
| 2012/0279314 A1 | 11/2012 | Hien |
| 2012/0286892 A1 | 11/2012 | de Luis |
| 2015/0276588 A1* | 10/2015 | Marshall ............ G01N 21/1717 250/343 |

FOREIGN PATENT DOCUMENTS

| | | |
|---|---|---|
| EP | 1370863 | 12/2003 |
| EP | 1510810 | 3/2005 |
| EP | 2533695 | 12/2012 |

OTHER PUBLICATIONS

Noland et al., "The Shape and Size of Hemozoin Crystals Distinguishes Diverse Plasmodium Species", Molecular and Biochemical Parasitology, vol. 130, No. 2, Aug. 31, 2003, pp. 91-99.

Sienkiewicz et al., "Multi-Frequency High-Field EPR Study of Iron Centers in Malarial Pigments", Journal of the American Chemical Society, vol. 128, No. 14, Apr. 12, 2006, pp. 4534-4535.

Song et al., "A Radio Frequency Device for Measurement of Minute Dielectric Property Changes in Microfluidic Channels", Applied Physics Letters, vol. 94, No. 2, Feb. 2009, pp. 023901(1)-023901(3).

Yang et al., "Distinguishing the Viability of a Single Yeast Cell with an Ultra-Sensitive Radio Frequency Sensor", Lab on a Chip, vol. 10, No. 5, Mar. 7, 2010, pp. 553-555.

Zhang et al., "Ferromagnetic Resonance of a Single Magnetic Nanowire Measured with an On-Chip Microwave Interferometer", Review of Scientific Instruments, vol. 82, No. 5, May 2011, pp. 054704(1)-054704(4).

* cited by examiner

HIGH SENSITIVITY TUNABLE RADIO FREQUENCY SENSORS

PRIORITY CLAIM

The present application claims the benefit of priority of U.S. Provisional Patent Application No. 61/859,868, titled High Sensitivity Tunable Radio Frequency Sensors, filed Jul. 30, 2014, which is incorporated herein by reference for all purposes.

GOVERNMENT SUPPORT CLAUSE

This invention was made with government support under ECCS-0925424 awarded by the National Science Foundation; 1K25GM100480-01A1 awarded by the National Institutes of Health; OPP1058477 awarded by the Gates Foundation and CHE-1152892 awarded by the National Science Foundation. The government has certain rights in the invention.

FIELD

The present subject matter relates generally to radio frequency (RF, from 3 KHz to 300 GHz) sensors. More particularly, the present subject matter relates to highly sensitive and highly tunable radio frequency (RF) sensors that can be used in conjunction with microfluidic channels.

BACKGROUND

Radio frequency (RF) sensors are used to characterize the electrical and magnetic properties of materials, including the properties of fluids, thin films, molecules, particles, biological cells, tissues and organs. For instance, RF sensors are critical for electron paramagnetic (spin) resonance spectrometers (EPR/ESR) and dielectric spectrometers (DS), including EPR/ESR and DS imaging systems. These sensors usually operate at transmission, reflection, or resonance modes. Existing RF sensors that cover a broad frequency range have low sensitivities. Those that have high sensitivities use resonators and operate at single frequencies or limited frequency points. Previous studies show a transmission coefficient as low as approximately −80 dB and a corresponding effective quality factor as high as approximately $10^4$ with liquid samples. The quality factor for such RF sensors needs to be further improved for applications like measuring single nano-particles, viruses, and molecules. Moreover, broadband operations are needed since many material properties need broadband RF measurements to investigate.

The use of a wide-band 180° splitter has helped to expand the operating frequencies of RF sensors. The frequency extension of such sensors, however, remains relatively modest and the sensor sensitivity is not much improved. Other approaches have achieved higher sensitivity but over a limited frequency range. For instance, dielectric resonators that operate with whispering-galley-modes have reported high quality factors, but only for a single resonant frequency. Moreover, the quality factor can be significantly reduced when lossy material-under-test (MUT), such as biochemical liquids, are introduced. Tunable RF resonators and harmonic-frequency/multi-mode resonator operations can help address the frequency limitation issue. The quality factors, however, remain limited.

Thus, a need exists for a simple RF sensor that can simultaneously provide both increased sensitivity and broadband frequency tuning capabilities.

SUMMARY

Aspects and advantages of the invention will be set forth in part in the following description, or may be obvious from the description, or may be learned through practice of the invention.

One exemplary aspect of the present disclosure is directed to EPR sensors including paired interferometers employing microfluidic channels to direct cells to be examined. The interferometers can include a reference branch and a test branch. The reference branch and the test branch have probing signals from a network analyzer through a signal splitter. In selected embodiments, a plurality of interferometers is provided and each of the interferometers is tunable over its own frequency band. In such embodiments, outputs from the plural interferometers may be combined to cover the desired frequency ranges in order to obtain additional information regarding cells passing through the microfluidic channels.

In another aspect, the present disclosure also relates to dielectric spectroscopy (DS) methods for analyzing cells and particles in order to obtain information relating to characteristics of such cells and particles. In accordance with such methods, information including, for example, the viability of cells may be obtained. In accordance with additional aspects of such methods, single cell analysis may be rapidly carried out to detect the presence of parasitized cells for diagnosis of, for example, malaria or other illnesses in an individual.

The present disclosure also relates to systems employing tunable radio-frequency (RF) sensors for automatic, rapid single-cell disease detection. For example, sensors constructed in accordance with the present technology can be used to count and characterize parasitized Red Blood Cells (PRBCs) in blood-plasma. Further, the sensors can measure finger tips non-invasively for rapid diagnosis.

Other exemplary aspects of the present disclosure are directed to the use of tunable attenuators and phase shifters in conjunction with RF sensors and providing time domain measurements using RF sensors.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1A:
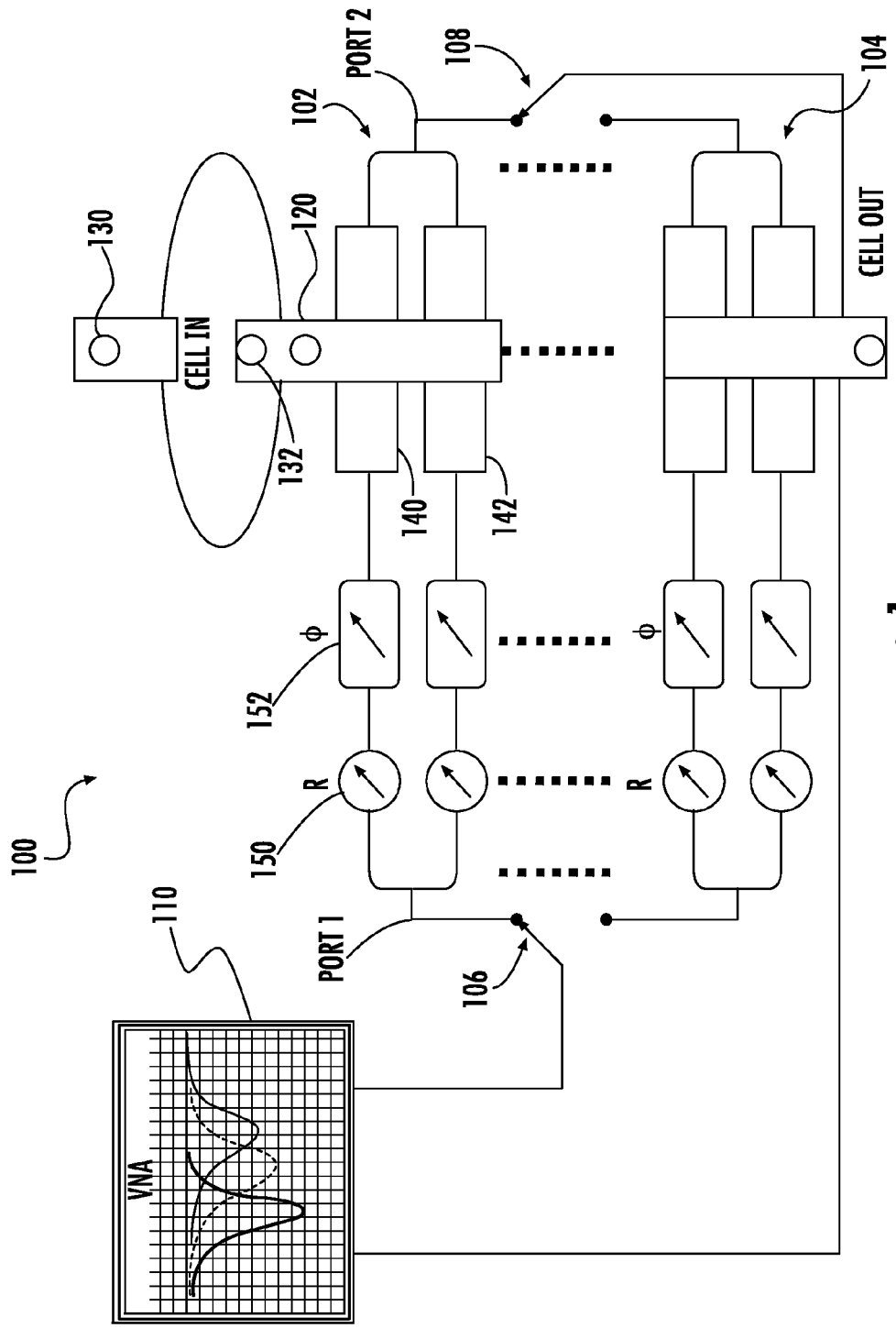
FIG. 1(a) illustrates a schematic block diagram of an RF sensor system according to an exemplary embodiment of the present disclosure.

Repeat use of reference characters throughout the present specification and appended drawings is intended to represent same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure relates to highly sensitive and tunable RF sensors. The RF sensors described herein simultaneously address the challenges of sensitivity and frequency tuning capabilities in a single sensor. The RF sensors are configured as tunable interferometers, which have two branches. In various embodiments, the two branches do not have to be identical. Cells or particles to be analyzed are passed through a microfluidic channel across waveguides corresponding to reference and test branches of the interferometers. More specifically, signals entering the RF sensor at a first port are divided by a first power divider or quadrature hybrid and sent through separate transmission lines. The signals are tuned using various tuning components, such as attenuators and phase shifters, to provide a defined phase shift and magnitude balance between the two branches.

In operation, a reference liquid can be passed through each microfluidic channel. Only one of the channels includes the cells or particles to be tested at the RF sensing electrodes and at a given time. The separated signals then exit corresponding channels and are recombined at a second power divider, or quadrature hybrid, and exit the RF sensor at a second port. A network analyzer can be configured to measure the transmission coefficient ($S_{21}$) to evaluate characteristics of cells passing through the microfluidic channel.

Additionally, a plurality of tunable interferometers may be employed, each operating in different frequency bands such that information obtain from the plurality of interferometers may be combined to provide further information.

Referring to the drawings, FIG. 1(a) illustrates a schematic block diagram of an RF sensor system 100 according to an exemplary embodiment of the present disclosure. The RF sensor system 100 corresponds to a plurality of interferometers 102, 104 that are selectively connectable by switches 106, 108 to a vector network analyzer (VNA) 110. Microfluidic channel 120 is configured to guide individual cells 130, 132 across coplanar waveguides 140, 142 representatively illustrated as a part of interferometer 102. In exemplary embodiments, the portion of the waveguides 140, 142 over which the microfluidic channel 120 passes may be constructed of gold. It should be appreciated that although a pair of interferometers 102, 104 is presently illustrated in FIG. 1(a), more or less than a pair of interferometers 102, 104 may be employed in other embodiments. Each pair of interferometers can be configured to operate in a different frequency band range. In certain embodiments, for example, three sensors each operating in different bands may be employed, such as from 20 MHz-1 GHz, 1 GHz-18 GHZ, and 18 GHz to 40 GHz. Those of ordinary skill in the art will clearly understand that switches 106, 108 should be configured to correspond to the total number of interferometers provided.

Still referring to FIG. 1(a), the tuning elements 150, 152 (variable attenuator and phase shifter, respectively) are coupled in series. Additionally, the tuning elements 150, 152 are coupled in series with the waveguide 140. Such tuning elements 150, 152 can provide amplitude and phase adjustability, respectively, for the waveguide 140. Further, each of the interferometers 102, 104 can be selectively connected via Port 1 and Port 2 through switches 106, 108, respectively, to corresponding input ports on the VNA 110. As such, energy in the form of a variable frequency signal from VNA 110 can be coupled to Port 1 and Port 2 of the interferometers 102, 104 corresponding to waveguides 140, 142. Further, one of the waveguides operates as a reference while the other waveguide corresponds to a "device under test" (DUT) for purposes of analyzing cells 130, 132 passing through microfluidic channel 120. It should be appreciated that channel 120 may also be provided as a nano-fluidic channel depending on the nature and size of the cells or particles to be analyzed.

Figure 1B:
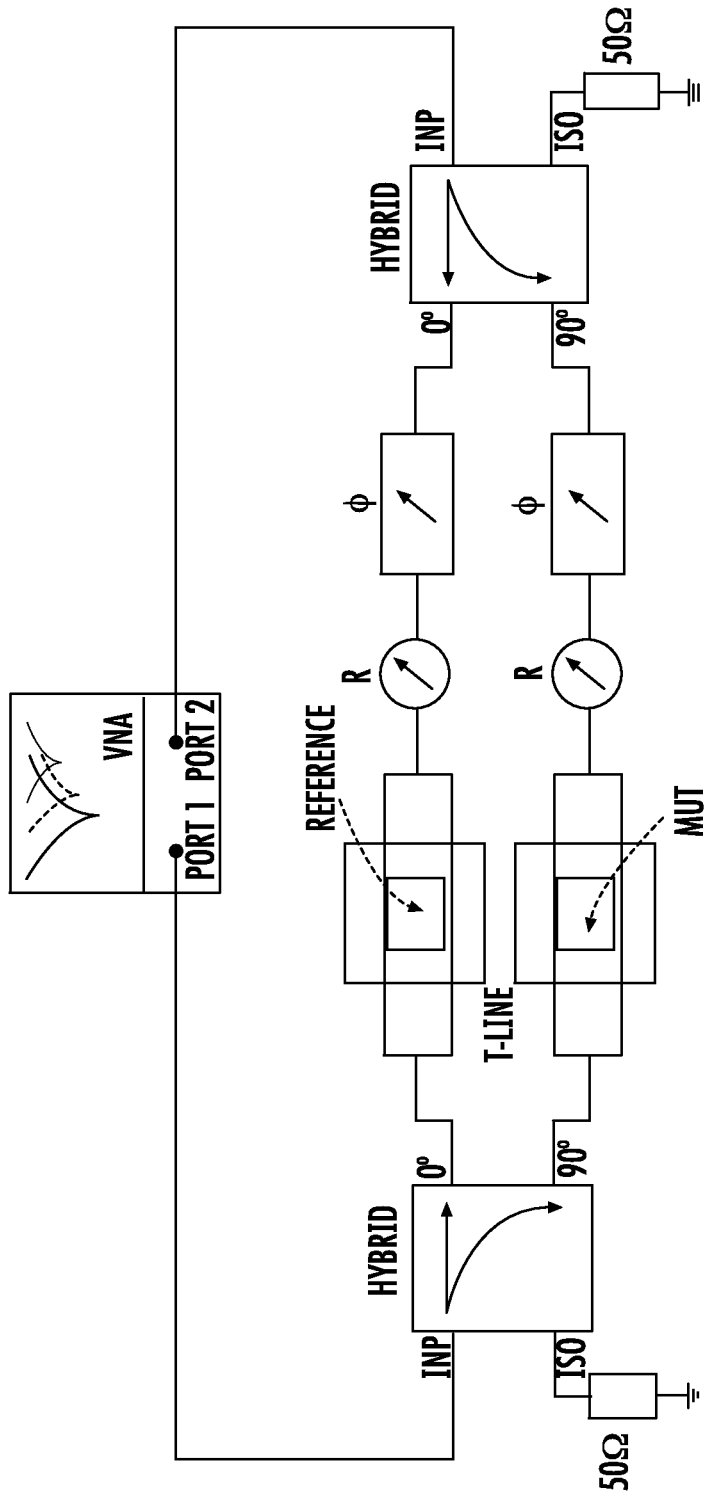
FIG. 1(b) illustrates a second schematic block diagram of an RF sensor system according to an exemplary embodiment of the present disclosure.

Referring now to FIG. 1(b), another schematic block diagram of an RF sensor system according to an exemplary embodiment of the present disclosure is illustrated. As shown, cells are passed through a microfluidic channel across waveguides corresponding to reference and test branches of the interferometers, as indicated by "Reference" and "MUT" (i.e. "Material-Under-Test"). The signals entering the RF sensor from Port 1 of the VNA are divided by the Hybrid and sent through separate transmission lines (T-Line). Further, the signals are tuned by the attenuators and phase shifters to provide a defined phase shift and magnitude balance between the two branches. In one embodiment, for example, a 180° phase difference is provided between the Reference and MUT branches to obtain high measurement sensitivity. More specifically, the 180° phase difference may be obtained by utilizing two 90° Hybrids. The signals are then recombined by a second Hybrid and enter the VNA at Port 2.

Figure 1C:
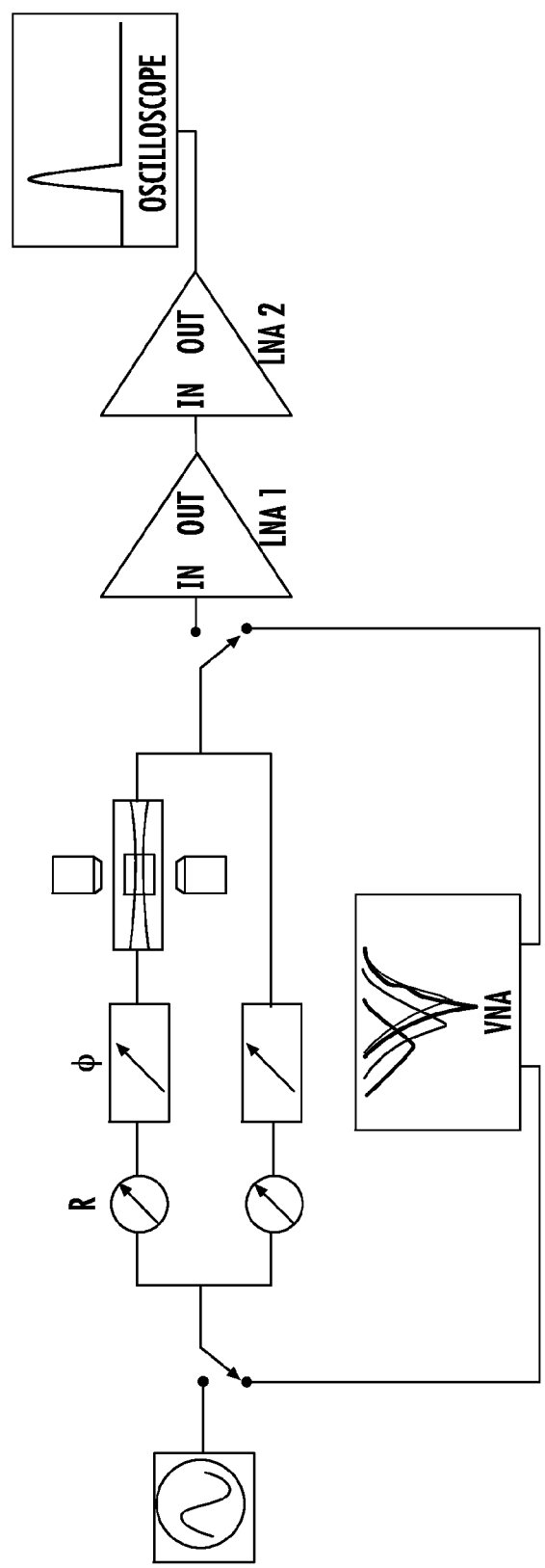
FIG. 1(c) illustrates a schematic block diagram of a time-domain embodiment of the present disclosure.
Figure 11:
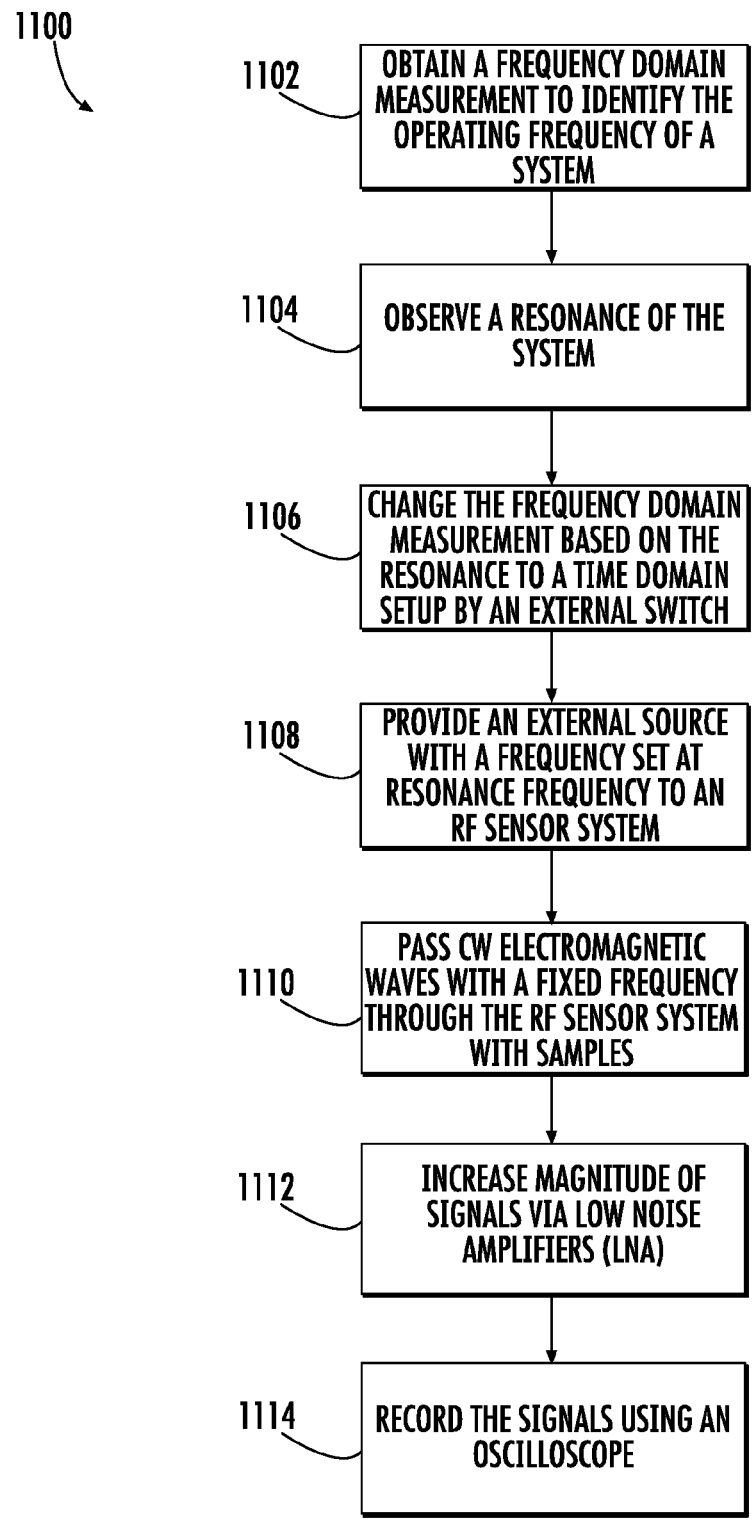
FIG. 11 illustrates a flow diagram of a method according to an exemplary embodiment of the present disclosure.

Referring now to FIG. 1(c) a schematic block diagram of a time-domain embodiment of the present disclosure and a corresponding method is illustrated. FIG. 11 depicts a flow diagram of an exemplary method 1100 according to the present disclosure for obtaining time-domain measurement using the system of FIG. 1(c) according to an exemplary embodiment of the present disclosure. FIG. 11 depicts steps performed in a particular order for purposes of illustration and discussion. Those of ordinary skill in the art, using the disclosures provided herein, will understand that various steps of the methods discussed herein can be omitted, rearranged, combined and/or adapted in various ways.

At (1102), a frequency domain measurement may be obtained to identify the operating frequency of a system. At (1104), a resonance of the system is observed. After observation, the frequency domain measurement may be changed or tuned to a time-domain setup by an external switch at (1106). At (1108), an external source may then be provided to an RF sensor system that is tuned to the resonance frequency. Additionally, in one embodiment, the VNA may include a variable frequency continuous wave (CW) source at (1110) such that electromagnetic waves may be passed with a fixed frequency through the RF sensor system having samples therein. At (1112), the magnitude of the signals from the VNA may be increased via Low Noise Amplifiers (LNA 1 and LNA 2). The signals may then be observed and recorded using an oscilloscope at (1114).

Figure 2:
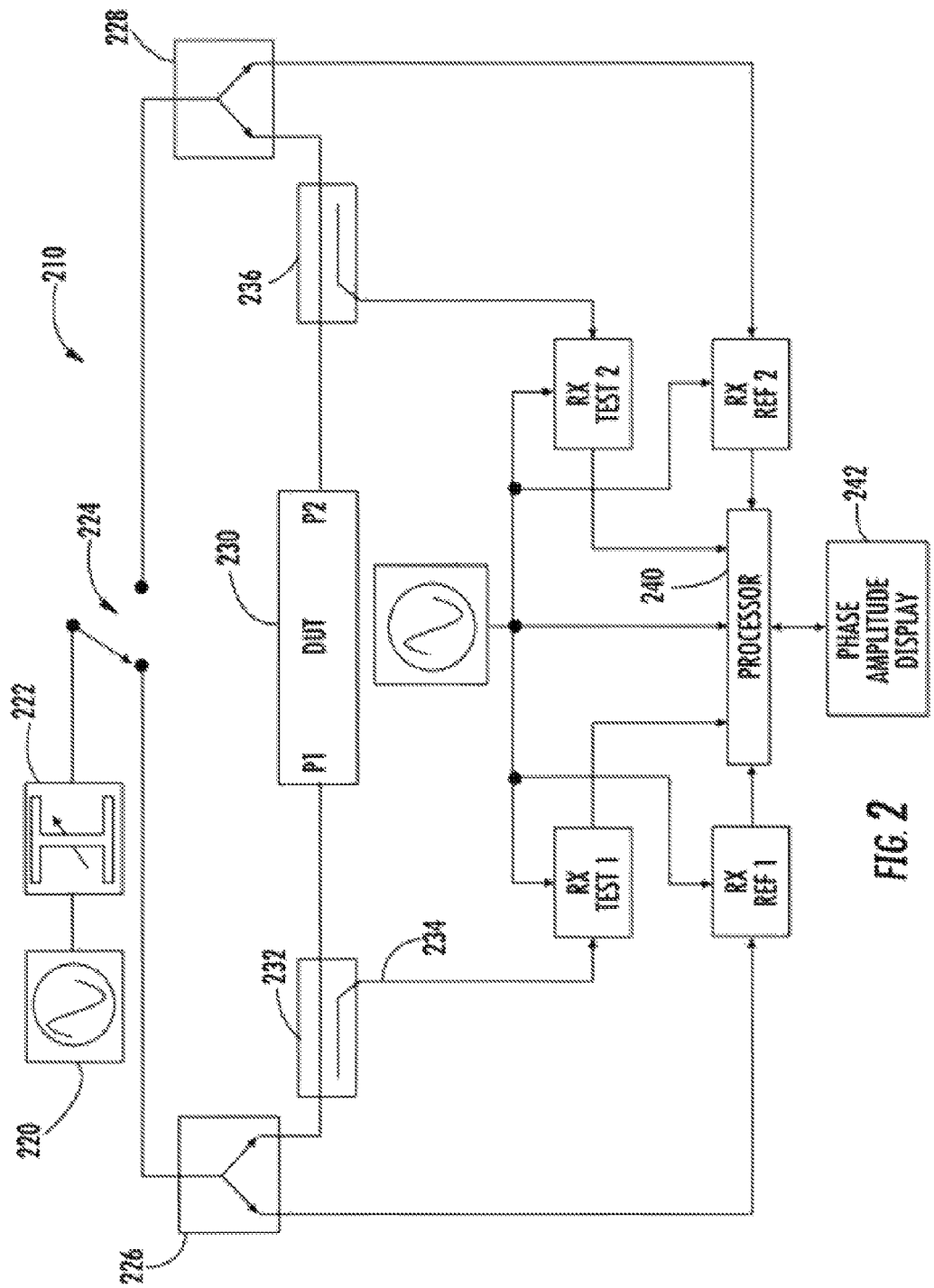
FIG. 2 illustrates a schematic block diagram of a Vector Network Analyzer (VNA) usable in combination with the RF sensors according to an exemplary embodiment of the present disclosure.

Referring to FIG. 2, a schematic block diagram of a VNA 210 usable in combination with the RF sensor 100 of FIG. 1(a) is illustrated. VNA 210 can be employed to measure both amplitude and phase properties. The basic architecture of the VNA includes a signal generator, a test set, one or more receivers and a display. Additionally, most VNAs have two test ports permitting measurement of four scattering parameters or S-parameters ($S_{11}$, $S_{21}$, $S_{12}$, $S_{22}$). In accordance with the present subject matter, the forward voltage gain $S_{21}$ vs. frequency is used to determine cell characteristics.

Still referring to FIG. 2, the VNA 210 includes a variable frequency continuous wave (CW) source 220 whose output can be coupled through level adjustment device 222 and then through selection switch 224 to one or more splitters 226, 228. As shown, the switch 224 can be positioned so as to direct the output of source 220 in a forward direction through DUT 230 to enable measurement of $S_{21}$. Splitter 226 can divide the applied signal from source 220 between a reference path including reference receiver RX REF 1 and a test channel to Port 1 (P1) of the DUT 230 via directional coupler 232. An additional outlet 234 of directional coupler 232 couples power reflected from Port 1 (P1) of DUT 230 to a test receiver RX TEST 1.

Similarly, signals leaving Port 2 (P2) are coupled via directional coupler 236 to test receiver RX TEST 2. All of the receivers may be coherent receivers and share a common reference oscillator. As is well understood by those of ordinary skill in the art, all of the complex receiver outputs are fed to a processor 240. The processor 240 can mathematically process and display the chosen parameters and format on phase and amplitude display 242. In one embodiment, the display 242 can show waveforms similar to that illustrated on VNA 110 of FIG. 1(a) as will be discussed in more detail below.

Figure 3:
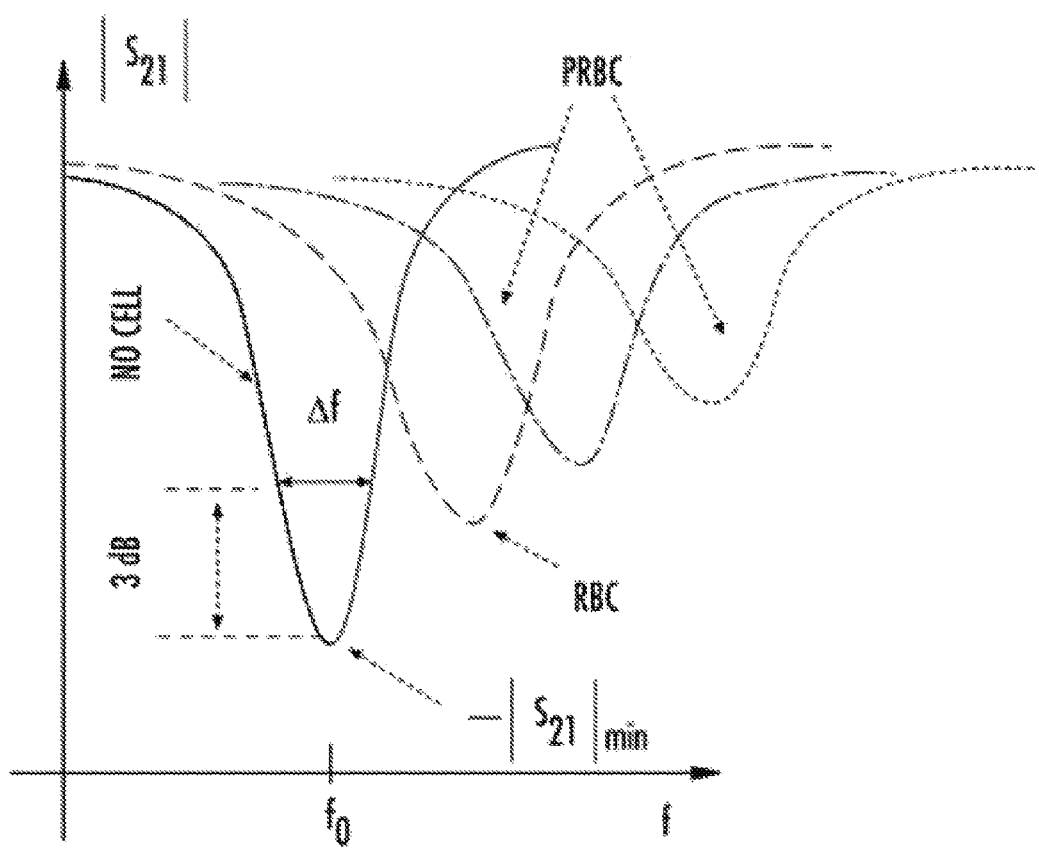
FIG. 3 illustrates a graph depicting forward voltage gain transmission coefficient magnitude ($S_{21}$) shifts produced by an RF sensor according to an exemplary embodiment of the present disclosure.

Referring now to FIG. 3, a graph illustrating transmission coefficient magnitude ($S_{21}$) shifts produced by an RF sensor in accordance with the present disclosure is illustrated. More specifically, the graph illustrates $S_{21}$ shifts produced by an RF sensor under various conditions. Based on the illustrated measurement results, an effective quality factor, $Q_e = f_0/\Delta f$, can be defined. For example, a 100 dB $|S_{21}|_{min}$ gives a $Q_e$ of approximately 106 at approximately 5 GHz. The exceptionally high $Q_e$ is a contributing factor for the high sensor sensitivity obtained from the RF sensors constructed in accordance with the present disclosure. Measurements in this exemplary embodiment were made using a coplanar waveguide (CPW) construction of the interferometer although micro-strip line construction can also be used.

Figure 4:
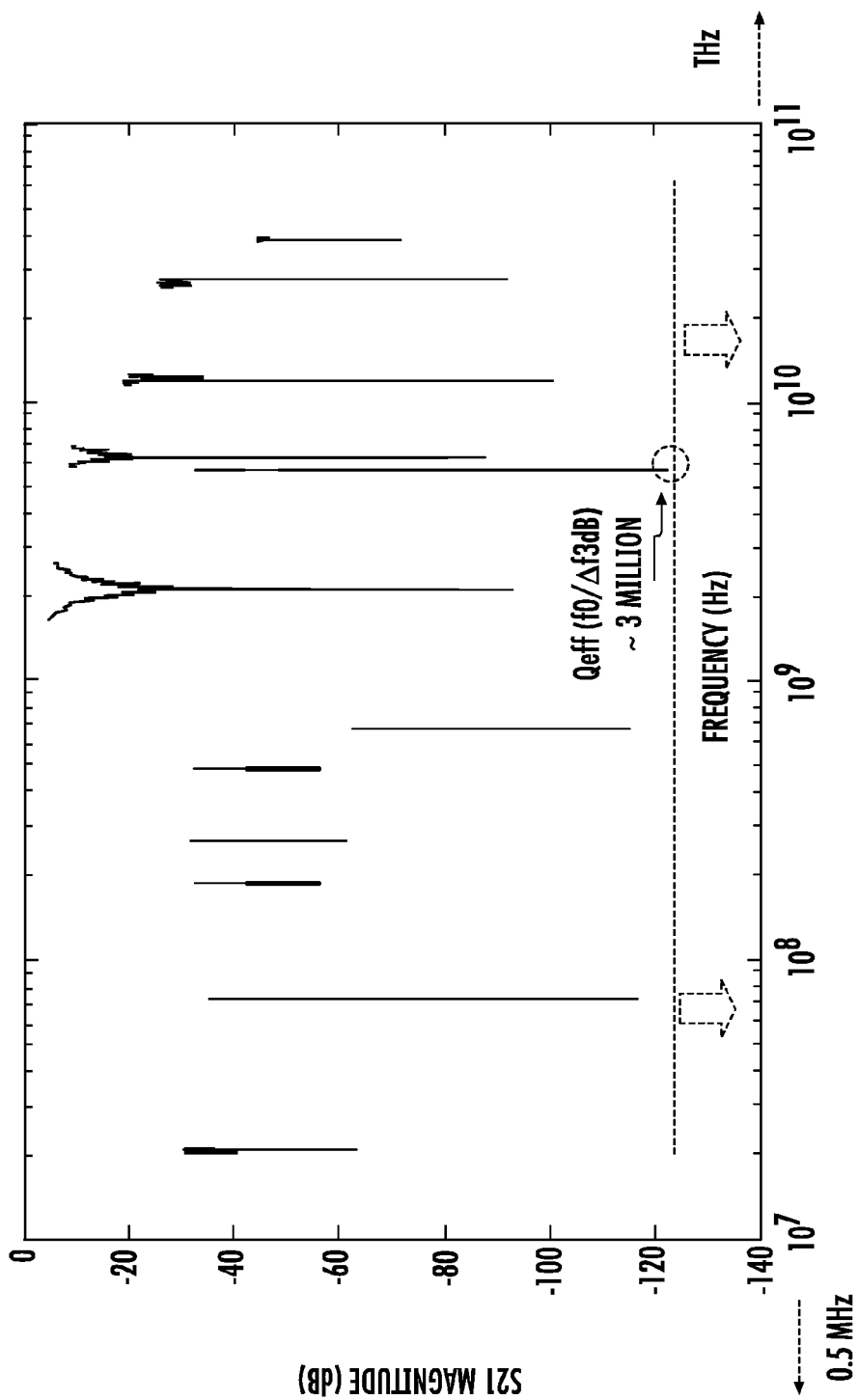
FIG. 4 illustrates a graph depicting measurement results obtained from an RF sensor according to the embodiment of FIG. 1(a)
Figure 5:
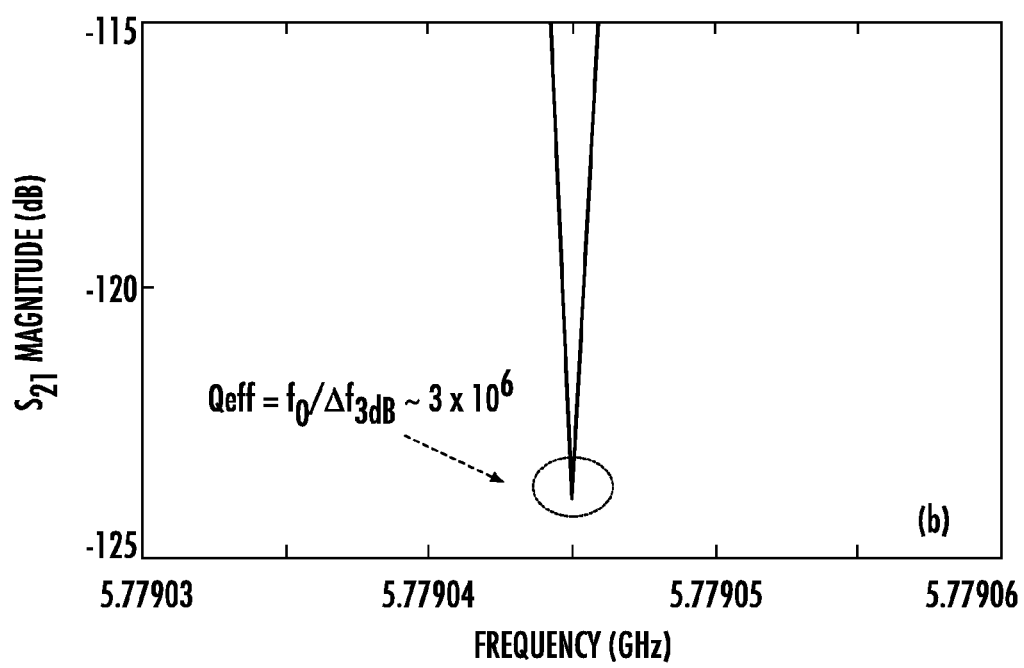
FIG. 5 illustrates a detailed view of a portion of FIG. 4 illustrating results of use of high effective quality factors.

Referring now to FIG. 4, a graph of measurement results obtained using an RF sensor constructed in accordance with the present disclosure is provided. As can be seen, the effective quality factor, $Q_{eff}(f_0/\Delta f3\text{ dB})$, is approximately 3 million. More specifically, FIG. 5 illustrates the measured $|S_{21}|_{min}$ from approximately 20.5 MHz to approximately 38 GHz. It is shown that $|S_{21}|_{min}$ values are very small, which indicates high sensitivity over the measured frequency range. The best $|S_{21}|_{min}$ is at approximately 6 GHz with $Q_{eff}$ approximately $3 \times 10^6$, which is much higher than conventional dielectric resonators. This $Q_{eff}$ is also comparable with that of conventional optical dielectric resonators, which have been developed for single molecule and single nanoparticle measurements. Nevertheless, the $|S_{21}|_{min}$ values are different for different frequencies. The differences are mainly caused by the manual tuning operations of the attenuators and phase shifters. With better tuning components and better control, it is expected that $|S_{21}|_{min}$ uniformity will be significantly improved across the operating frequency ranges.

Figure 6:
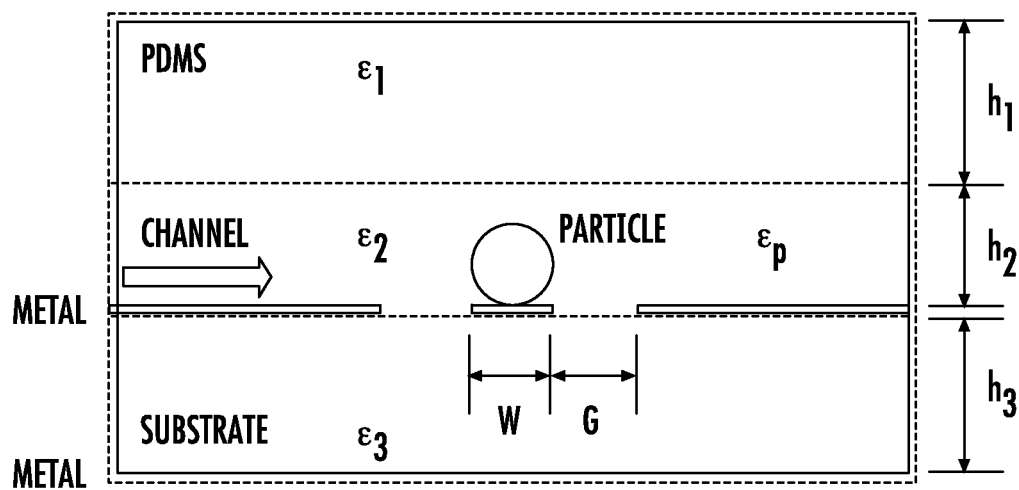
FIG. 6 illustrates a cross sectional view of a coplanar waveguide (CPW) measurement channel according to an exemplary embodiment of the present disclosure.

Referring now to FIG. 6, a cross sectional view of a measurement channel constructed in accordance with the present subject matter is illustrated. In accordance with one embodiment, the upper $h_1$ layer may be constructed from a polydimethylsiloxane (PDMS) polymer. The lower $h_3$ layer can be constructed from various materials including, without limitation, glass, quartz and/or silicon. The signal line portion of a coplanar waveguide is illustrated with width W while gaps of width G are provided between the signal line and coplanar ground or reference conductors. In some embodiments of the present disclosure, the upper $h_1$ layer can be at least partially omitted leaving an open channel to form an open sample holder. In such instances fluidic flow may be optional.

Various parameters of the particle can be determined as follows. For instance, the effective permittivity of the $h_2$ channel can be computed as follows:

$$\epsilon_{\mathit{eff}} = (\epsilon_{\mathit{eff\text{-}total}} - q_1\epsilon_1 - q_3\epsilon_3)/q_2$$

$q_1$ are the filling factors
The permittivity of the particle can be determined as follows:

$$\epsilon_p = (\epsilon_{\mathit{eff}} - S_2\epsilon_2)/S_P$$

$S_p$: particle cross section area, $S_2$: the remaining area
The propagation constant $\gamma$ can be determined as follows:

$$t_{21} = S_{21,MUT} + S_{21,REF}$$
$$S_{21,REF} = e^{-\gamma_o l}\ \gamma_o = \alpha_o + j\beta_o$$
$$S_{21,MUT} = e^{-\gamma l} = e^{-\gamma_o l} = e^{-\gamma_o l}e^{-(\delta\alpha + j\delta\beta)l}$$

$$T_{21,REF}\text{ (dB)} = 20\ \log_{10}|Ae^{-\gamma_o l_o}(1 - e^{-(\Delta\alpha_o + j\beta_o)\Delta l_o})| = 20\ \log_{10}|p(1 - q)|$$
$$T_{21,MUT}\text{ (dB)} - T_{21,REF}\text{ (dB)} = 20\ \log_{10}|(1 - qe^{-\delta\alpha l}e^{-j\delta\beta l})/(1 - q)|$$
$$\gamma = (\alpha_o + \delta\alpha) + j(\beta_o + \delta\beta)\text{ are obtained from transmission coefficients}$$

The parameters p and q correspond to attenuator and phase shifter settings, respectively.

The propagation constant can be used to determine the real and imaginary components of the permittivity of the particle $\in_{eff}=\in'_{eff}-j\in''_{eff}$ as well as the real and imaginary components of the permeability of the particle $\mu_{eff}=\mu'_{eff}-j\mu''_{eff}$.

Figure 7:
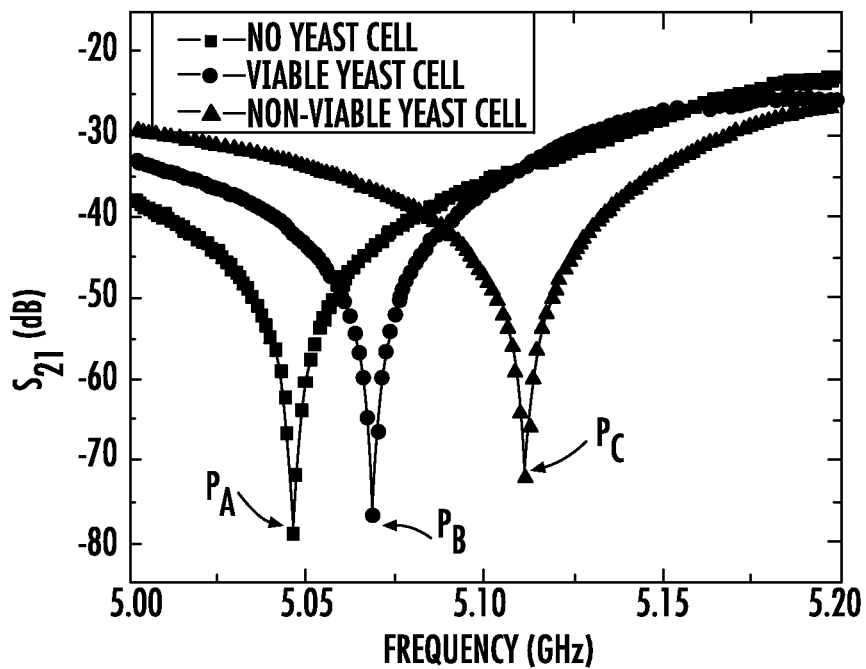
FIG. 7 illustrates a graph depicting measurement results of single yeast cells using an RF sensor according to an exemplary embodiment of the present disclosure.

Referring now to FIG. 7, a graph illustrating measurement results of a plurality of single yeast cells using an RF sensor, such as an electron-paramagnetic-resonance (EPR) sensor, in accordance with the present subject matter is illustrated. As shown, the forward voltage gain transmission coefficient magnitude $S_{21}$ shifts depending on not only the presence of a cell, but also the viability of any cell present. Thus, for example with no cell present ($P_A$), the detected frequency and corresponding $S_{21}$ measurement are lower than those of a viable cell ($P_B$). Similarly, the viable cell measurements ($P_B$) are also lower than non-viable yeast cell measurements ($P_C$). As indicated by the test results, the high speed identification and characterization of various cells is greatly enhanced through the implementation of EPR sensors in accordance with the present technology.

Figure 8:
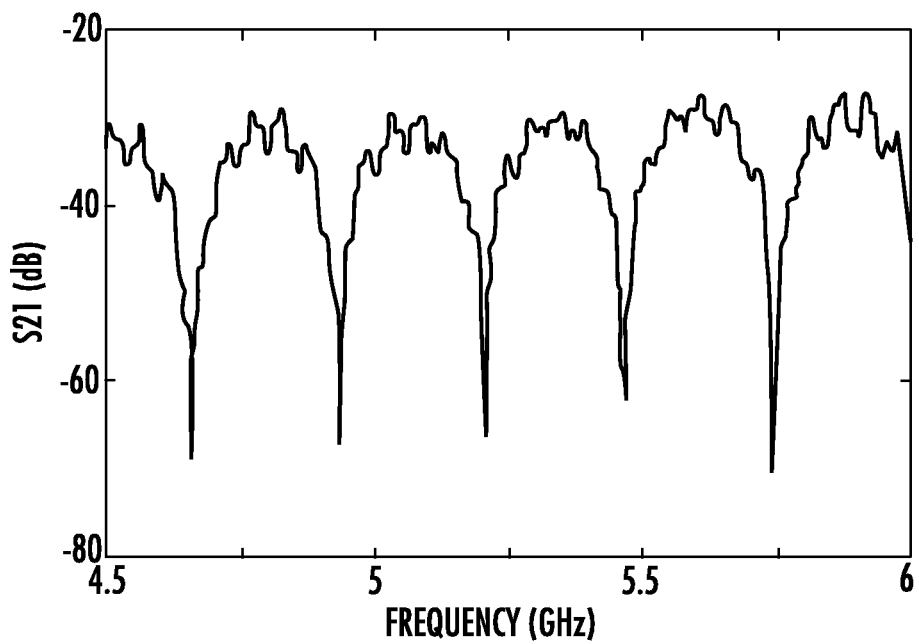
FIG. 8 illustrates a graph depicting measurement results of a multi-frequency RF sensor according to an exemplary embodiment of the present disclosure.

With reference now to FIG. 8, a graph illustrating measurement results of a multi-frequency RF sensor, such as an EPR sensor, in accordance with the present subject matter is illustrated. As may be recalled with respect to FIG. 1(*a*), a plurality of interferometer pairs can be provided and selectively coupled to the VNA 110. Such interferometers may be configured to operate in different frequency ranges and may be "tuned" by respective attenuators and phase shifters in order to obtain significantly more cell information based on harmonic frequencies produced by the multi-frequency EPR sensors. In certain embodiments, for example, three sensors each operating in different bands may be employed, such as from 20 MHz-1 GHz, 1 GHz-18 GHZ, and 18 GHz to 40 GHz. Using such techniques, other cell properties such as cell viability discussed with respect to FIG. 7, can be obtained for other disease diagnostics and analysis at the single cell level. By providing passive tuning elements, the minimum value of the forward voltage gain $S_{21}$ may be increased to 80 dB or better at each harmonic frequency point. Eight or more such harmonic points may be produced based on the number of frequency ranges provided.

Experimental Results

To investigate the sensor sensitivity and frequency tunability, 50Ω coplanar waveguides (CPW) and microstrip lines were used for the T-lines in FIG. 1(*a*). Polydimethylsiloxane (PDMS) wells were glued to the T-lines to hold de-ionized (DI) water, which is used as the MUT and reference solutions. The mismatches between the MUT and reference branches were minimized by adjusting the attenuators and phase shifters. As mentioned, FIG. 4 representatively illustrates the measured $|S_{21}|$ from approximately 20.5 MHz to approximately 38 GHz. As illustrated in FIG. 5, it was found that $|S_{21}|_{min}$ values are very small, which indicates high sensitivity over the measured frequency range. The best $|S_{21}|_{min}$ is at approximately 6 GHz with $Q_{eff}$ approximately $3 \times 10^6$, which is much higher than that reported for dielectric resonators. such a $Q_{eff}$ value is also comparable with that of the optical dielectric resonators, which have been developed for single molecule and single nanoparticle measurements. Nevertheless, the $|S_{21}|_{min}$ values are different for different frequencies. The differences are mainly caused by the manual tuning operations of the attenuators and phase shifters. With further improvements in tuning components and control, it should be expected that $|S_{21}|_{min}$ uniformity will be significantly improved across the operating frequency ranges.

It should be pointed out that $|S_{21}|_{min}$ values and their corresponding frequencies, $f_0$, fluctuate and drift with time when the RF sensor is tuned for high sensitivity operations, e.g. when $|S_{21}|_{min}<-100$ dB. As a result, the high sensitivity operations in FIG. 5 are only obtained for a time frame of approximately 1-2 minutes. To obtain quantitative values of MUT permittivity, $f_0$ shifts and $|S_{21}|_{min}$ changes were studied provided that the geometries and dimensions of the T-lines, sample holders and sample volumes were given. In the experimental tests, 2-proponal-water solution of 0.01 mole fraction was the MUT. The MUT was placed in a PDMS well, which was glued to a CPW. The PDMS well was 11 millimeters (mm) high, 25.4 mm wide, and 3 mm long along the CPW line. A plastic cylindrical tube is used to hold the DI water as reference on the second T-line, which is an identical CPW. The 50Ω CPW signal lines were 2 mm wide and built with Duroid 5870 substrates. The focus of the measurements was on frequency band II, from approximately 1 GHz to approximately 12 GHz, where better tuning components as well as discrete standards for VNA calibration were observed.

To measure the permittivity of 2-proponal-water solution, the sensor sensitivity $|S_{21}|_{min}$ is intentionally tuned to approximately -60 dB approximately -70 dB, instead of higher sensitivity operation status, for a few reasons. First, the sensitivity is reasonable for measuring 2-propanol-water solutions at our targeted concentration levels, which are of interest in many other efforts. Second, higher sensitivity would require stricter sample handling procedures than simple syringe operations, which are conveniently available. Third, the relatively lower sensitivity does not affect the development of the experimental procedures and data process algorithms.

The following equations, obtained from analyzing signal transmission through the sensors, can be used to calculate $\gamma_p = \alpha_p + j\beta_p$, the propagation constant of MUT section when 2-propanol-water solution is included:

$$(S_{21(m)}-S_{21(w)})/(S_{21(p)}-S_{21(w)})=(\exp(-\gamma_m)-\exp(-\gamma_w))/(\exp(-\gamma_p)-\exp(-\gamma_w))$$

where subscript m is for methanol-water solution, p for 2-propanol-water solution, and w for water-water measurement. The parameters $\gamma_m$, p, w are the corresponding propagation constants. Once $\gamma p = \alpha p + j\beta p$ is obtained, the real and imaginary permittivity components of 2-propanol water solution, $\in = \in' - j \in''$, can be obtained through the following equations.

$$\alpha_p = \pi \alpha_1 \in_1^* / (\lambda_0 \sqrt{(\alpha_0 - \alpha_1 + \alpha_1 \in_1' + \alpha_2 \in_2')(\alpha_0 + \alpha_2)})$$

$$\beta_p = 2\pi f \sqrt{\in_0 \mu_0} \sqrt{(\alpha_0 - \alpha_1 + \alpha_1 \in_1' + \alpha_2 \in_2')/(\alpha_0 + \alpha_2)}$$

where $a_i = 2\in_o K((k_i)/K(k_i'))$, $i=0, 2$, $a_1 = 2\in_0 K(k_1')/K(k_1)$, $K(k)$ is the complete elliptic integrals of the first kind with modulus k, and $k' = \sqrt{1-k^2}$. Additionally, $k_0$, $k_1$, and $k_2$ can be obtained using the following equations:

$$k_0 = w/(w+2g)$$

$$k_1 = \sin h(\pi w/4h_1)/\sin h(\pi(w+2g)/4h_1)$$

$$k_2 = \tan h(\pi w/4h_2)/\tan h(\pi(w+2g)/4h_2)$$

where the geometrical parameters are defined in FIG. 8.

Figure 9:
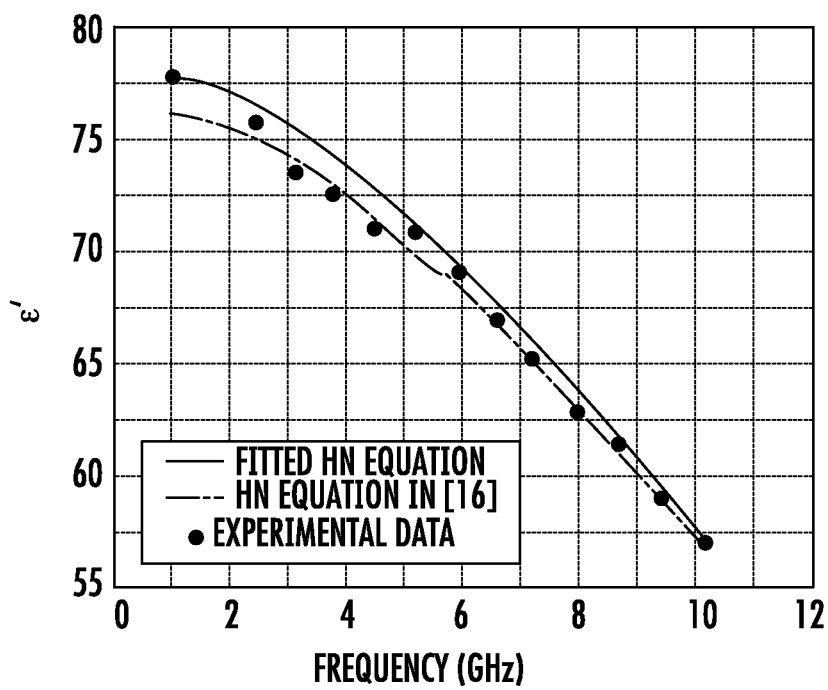
FIG. 9 illustrates a graph of experimentally obtained permittivity of 2-proponal-water mixture according to an exemplary embodiment of the present disclosure.
Figure 10:
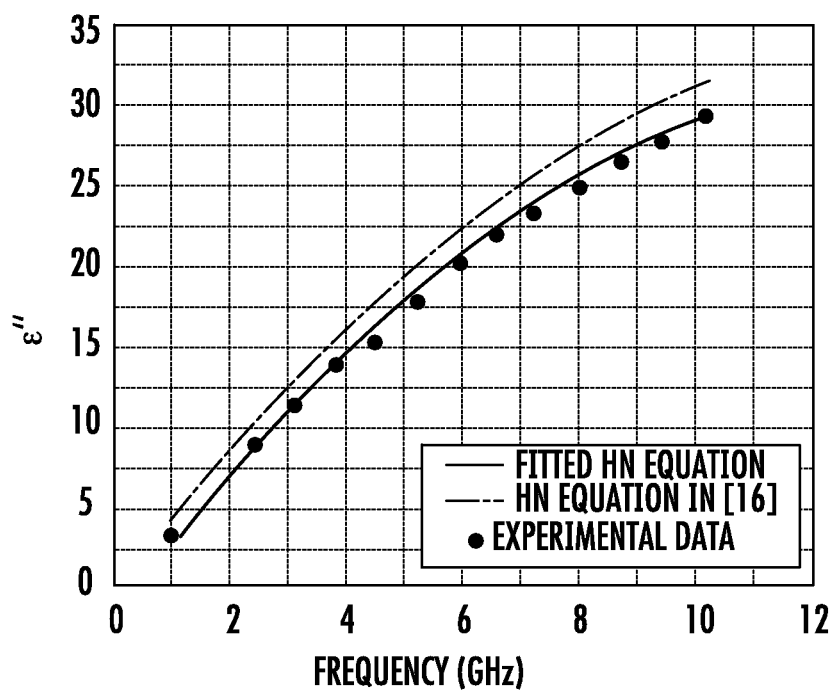
FIG. 10 illustrates another graph of experimentally obtained permittivity of 2-proponal-water mixture according to an exemplary embodiment of the present disclosure.

FIGS. 9 and 10 graphically illustrate the experimentally obtained permittivity $\in$ of 2-proponal-water mixture using the apparatus of the present subject matter. The dots represent the experimental data obtained for permittivity $\in$. The solid lines represent the permittivity $\in$ calculated using the "Havriliak-Negami (FIN) equation" as shown below:

$$\in^*(f) = \in_\infty + \Delta\in/(1+(i2\pi f\tau)^\beta)^\alpha$$

where $\in_\infty$ is solution permittivity at infinite frequency, $\Delta\in$ is the permittivity change between high and low frequencies, $\tau$ is the relaxation time, and $\alpha$ and $\beta$ are fitting constants. As shown, $\in'$ decreases with frequency, whereas $\in''$ increases with frequency.

The present disclosure has significant applicability in the development of portable, quantitative and highly sensitive RF diagnostic tools that are easy to operate and rugged to deploy. Such tools can be used to count and characterize parasitized RBCs (PRBCs) in blood-plasma and measure finger tips non-invasively for rapid malaria diagnosis. Of course the RF sensor constructed in accordance with the present disclosure is not limited to any particular diagnoses, but may be used to evaluate characteristics of a large variety of cells and particles.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An RF sensor for a material under test, comprising:
a plurality of interferometers, each interferometer comprising one or more fluidic channels each disposed across a reference branch and a test branch; the reference branch comprising a first waveguide and the test branch comprising a second waveguide;
a first port associated with each of the plurality of interferometers, the first port configured to separate signals between a first transmission line and a second transmission line, the first transmission line operable to provide a reference RF signal to the first waveguide and the second transmission line operable to provide a test RF signal to the second waveguide;
a second port associated with each of the plurality of interferometers, the second port configured to recombine signals from the first transmission line and the second transmission line;
a signal analyzer coupled to the first port and the second port of each of the plurality of interferometers, the signal analyzer operable to measure one or more scattering parameters;
wherein each of the plurality of interferometers is associated with a different frequency band range.

2. The RF sensor of claim 1, wherein the signal analyzer is operable to provide RF energy associated with a different frequency band to each of the plurality of interferometers.

3. The RF sensor of claim 1, wherein the plurality of interferometers comprise a first interferometer associated with a frequency band of 20 MHz to 1 GHz, a second interferometer associated with a frequency band of 1 GHz to 18 GHz, and a third interferometer associated with a frequency band of 18 GHz to 40 GHz.

4. The RF sensor of claim 1, wherein the one or more scattering parameters comprise a voltage gain transmission coefficient $|S_{21}|$.

5. The RF sensor of claim 1, wherein the one or more fluidic channels comprise a microfluidic channel or a nanofluidic channel.

6. The RF sensor of claim 1, wherein the one or more fluidic channels comprise gold.

7. The RF sensor of claim 1, wherein the first transmission line and second transmission line comprise one or more tuning elements coupled in series with the respective first and second waveguides.

8. The RF sensor of claim 7, wherein the one or more tuning elements comprise an attenuator circuit.

9. The RF sensor of claim 7, wherein the one or more tuning elements comprise a phase shift circuit.

10. The RF sensor of claim 1, wherein the test RF signal has a 180° phase difference relative to the reference RF signal.

11. The RF sensor of claim 10, wherein each interferometer comprises two 90° hybrid circuits.

12. The RF sensor of claim 1, wherein the signal analyzer is a variable network analyzer.

13. The RF sensor of claim 1, wherein the plurality of interferometers are selectively couplable to the signal analyzer by one or more switches.

14. The RF sensor of claim 1, wherein the material under test comprises a biological cell.

15. The RF sensor of claim 1, wherein the first waveguide and the second waveguide are coplanar waveguides.

16. The RF sensor of claim 1, wherein the first waveguide and the second waveguide are microstrip waveguides.

17. The RF sensor of claim 1, wherein the signal analyzer comprises one or more processors and a display, the one or more processors operable to provide a waveform associated with the one or more scattering parameters for display on a display device.

* * * * *

UNITED STATES PATENT AND TRADEMARK OFFICE
CERTIFICATE OF CORRECTION

PATENT NO. : 9,464,994 B2
APPLICATION NO. : 14/445433
DATED : October 11, 2016
INVENTOR(S) : Pingshan Wang et al.

Page 1 of 1

It is certified that error appears in the above-identified patent and that said Letters Patent is hereby corrected as shown below:

On the Title Page

Item (56) under the heading "FOREIGN PATENT DOCUMENTS":
The first cited reference currently reads "EM 2486416" should read "EP 2486416"

Signed and Sealed this
Eighteenth Day of June, 2019

Andrei Iancu
*Director of the United States Patent and Trademark Office*